United States Patent [19]

Nomura et al.

[11] Patent Number: 5,726,052
[45] Date of Patent: Mar. 10, 1998

[54] RESTRICTION ENDONUCLEASE

[75] Inventors: Yoshiko Nomura, Kyoto; Yoshizumi Ishino, Takatsuki; Ikunoshin Kato, Uji, all of Japan

[73] Assignee: Takara Shuzo Co., Ltd., Kyoto-fu, Japan

[21] Appl. No.: 507,615

[22] Filed: Jul. 26, 1995

[30] Foreign Application Priority Data

Jul. 28, 1994 [JP] Japan ................................. 6-194602

[51] Int. Cl.$^6$ ................................. C12P 19/34; C12N 9/22
[52] U.S. Cl. ................................. 435/199; 435/6; 435/91; 435/253.5; 435/886
[58] Field of Search ................................. 435/199, 6, 91, 435/886, 253.5

[56] References Cited

U.S. PATENT DOCUMENTS

| | | | |
|---|---|---|---|
| 4,840,901 | 6/1989 | Grosskopf et al. | 435/199 |
| 4,935,357 | 6/1990 | Suzybaski | 435/199 |
| 4,975,376 | 12/1990 | Bolton et al. | 435/199 |
| 5,120,651 | 6/1992 | Yamada et al. | 435/199 |
| 5,134,069 | 7/1992 | Kaluza et al. | 435/199 |
| 5,300,432 | 4/1994 | Simcox et al. | 435/886 |
| 5,391,487 | 2/1995 | Kappelman et al. | 435/886 |
| 5,496,717 | 3/1996 | Nomura et al. | 435/199 |

FOREIGN PATENT DOCUMENTS 0 464 990 A3  1/1992  European Pat. Off. .

OTHER PUBLICATIONS

Molecular Sigma Biology Catalog, 1992 pp. 16, 25, 34, 35.
Housekin no doutei jikkenhou (Experimental methods for the identification of actinomycetes), first edition, by The Society for Actinomycetes, Japan, (The Secretariat of The Society for Actinomycetes, Japan, 1985), pp. 58–87 and 131–139.
Biseibutu no kagaku bunrui jikkenhou (Experimental method for chemical classification of microorganisms), first edition, by K. Komagata (Gakkai syuppan center 1982), pp. 143–155.
Atarashii bunruigaku ni hansou suru saikin douteihou (Identification of microorganisms under new taxonomy), first edition, by E. Yabuuti et al., (Natane syuppan, 1987), pp. 79–81.

*Primary Examiner*—Herbert J. Lilling
*Attorney, Agent, or Firm*—Wenderoth, Lind & Ponack

[57] ABSTRACT

A restriction endonuclease which recognizes the nucleotide sequence of the following Chemical formula 1 in double stranded DNA and strictly cleaves the nucleotide sequence at the sites marked by arrows.

Chemical formula 1

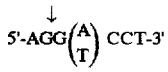

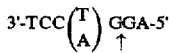

The endonuclease may be made cultivating a strain of the genus Streptomyces such as Streptomyces sp. YH 8647 (FERM BP-5022) capable of producing it.

4 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 253 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:1:

```
AACCTACACC AGTGTAAAAG AGGTATCTTT TGTGTGGTCA AGCAGGCCAA ACTTACCTAC      60
GAAAAAACCA CTACCGGCAA CCGCCTCAGC TACAAGCTAC CCACCCAGCG CCAAAAACTG     120
GTGCTTATGG TGGGAGAAAA ACCTATCACC GTCACCCAGC ACTCGGCAGA AACAGAGGGC     180
TGCCTGCACT TCCCCTATCA GGGTCCAGAG GACCTCTGCA CTCTTATTAA AACCATGTGT     240
GGTATTAGAG ATC                                                        253
```

( 2 ) INFORMATION FOR SEQ ID NO:2:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: Other nucleic acid (synthetic acid)

( x i ) SEQUENCE DESCRIPTION: SEQ ID NO:2:

```
GTTTTCCCAG TCACGAC    17
```

RESTRICTION ENDONUCLEASE

BACKGROUND OF THE INVENTION

1. Field of the Invention

This invention relates to a Class-II restriction endonuclease which recognizes a strict sequence of seven bases in a double stranded deoxyribonucleic acid (DNA) molecule and cleaves said DNA molecule at such site.

2. Description of Related Art

Restriction endonucleases are endonucleases which recognize a specific sequence of bases in a DNA molecule and cleave the DNA strands at specific sites. Many kinds of restriction endonucleases have so far been found. As a result of the progress in molecular genetics and biochemistry, DNA was proven to be the carrier of genetic information, and since then restriction endonucleases have been extensively used for various purposes, such as in the clarification of genetic diseases in gene manipulation.

Among them, class II restriction endonucleases, which can recognize a specific DNA sequence and digest the DNA strand specifically within the sequence, are especially important and essentially used in genetic engineering techniques.

More than 300 class II restriction endonucleases have been isolated, however, many DNA sequences having no cognate restriction endonucleases (can not be recognized by any known restriction endonuclease) still remain. Therefore, novel class II restriction endonucleases are needed having ability to recognize and digest these sequences, so that researchers have more chance to cut their DNA at positions suitable for each experiment.

Moreover, restriction endonucleases with low cutting frequencies are more convenient for structural analyses of high molecular weight DNA such as genome analysis projects of several living things, and the discovery of the class II restriction endonucleases recognizing long DNA sequences more than six bases have been demanded.

SUMMARY OF THE INVENTION

The purpose of this invention is to provide a novel restriction endonuclease of class II having an ability to recognize and cut a new DNA sequence, which is suitable for genetic engineering research including the analysis of high molecular weight DNA.

In a first aspect of this invention, there is provided a restriction endonuclease which strictly recognizes the nucleotide sequence of the following Chemical formula 1 in a DNA molecule and strictly cleaves the nucleotide sequence at the sites marked by arrows.

Chemical formula 1 wherein A, G, T and C represent adenine, guanine, thymine and cytosine, respectively.

In a second aspect of the this invention, there is provided a process for producing the above restriction endonuclease, which comprises growing a microorganism belonging to the genus Streptomyces having all the identifying characteristics of Streptomyces sp. YH8647 (FERM BP-5022) and which produces the above restriction endonuclease and recovering the restriction endonuclease thus formed from the culture broth.

DETAILED DESCRIPTION OF THE PREFERRED EMBODIMENT

The Class-II restriction endonuclease of this invention may be any restriction endonuclease which strictly recognizes and cleaves the above-mentioned nucleotide sequence, which restriction endonuclease can be obtained by cultivating a strain which produces the restriction endonuclease, a mutant of the above strain, or a recombinant prepared by isolating the gene encoding the production of the said restriction endonuclease and transforming it into a different kind of host organism by utilizing ordinary genetic manipulation techniques.

The actual strain producing the restriction endonuclease that recognizes the heptanucleotide sequence described above is Streptomyces sp. YH8647. This strain was isolated from soil which were collected and stored in inventors laboratories. The bacteriological characteristics are shown in Table 1.

TABLE 1

| Type of cell wall | Type I |
|---|---|
| L, L-diaminopimelic acid | + |
| meso-diaminopimelic acid | − |
| diaminobutyric acid | − |
| glycine | + |
| aspartic acid | − |
| ornithine | − |
| lysine | − |
| arabinose*[1] | − |
| galactose*[1] | + |
| Quinone | MK-9(H$_8$), MK-9(H$_6$) |
| Aerial mycelium*[2] | + |
| Spore linkage*[2] | + |

*[1]Assumption by hydrolysis of the whole cells with sulfuric acid.
*[2]Examination through a microscope.

The analysis of the cell wall composition was performed as described in the following three literatures; (1) *Housenkin no doutei jikkenhou* (first edition; Experimental methods for the identification of actinomyces) by The Society for Actinomycetes, Japan (The Secretariat of The Society for Actinomycetes, Japan, 1985); (2) *Biseibutu no kagaku bunrui jikkenhou* (first edition; Experimental methods for chemical classification of microorganisms) by K. Komagata (Gakkai syuppan center, 1982); and (3) *Atarashii bunruigaku ni bansou suru saikin douteihou* (first edition; identification of microorganisms under new taxonomy) by E. Yabuuti et al., (Saikon syuppan, 1987). The cell wall type of this strain was concluded to be type I. The analyses of the quinone component showed that this strain has menaquinones having 9 isoprene units with 6 or 8 of the saturated hydrogen in the multiprenyl strand. Moreover, from the morphological observation, the strain has aerial mycelium and spore linkage. From these analyses, this strain was identified as a species belonging to the genus Streptomyces.

The present strain was designated as Streptomyces sp. YH8647. This strain was deposited on Sep. 29, 1993 at National institute of Bioscience and Human-Technology Agency of Industrial Science and Technology (1–3, Higashi 1 chome Tsukuba-shi Ibaraki-ken 305, JAPAN) in accordance with the Budapest Treaty under the accession number FERM BP-5022.

The restriction endonuclease isolated from Streptomyces sp. YH8647 with recognition sequence of the seven bases has the properties as described above and is designated Sse 8647I.

Detailed below is the process for producing restriction endonuclease Sse 8647I.

Any nutrients which the strain used assimilates to produce Sse 8647I may be added to the culture medium. Glucose, maltose, glycerol and others may be used as carbon source, while yeast extract, peptone, corn steep liquor, bouillon and others are suitable as nitrogen source. In addition, minerals and metal salts, such as phosphates, potassium salts and magnesium salts, may also be added.

The yield of Sse 8647I varies depending on culture conditions. Good results are generally obtained at a temperature in the range from 20° to 35° C. and at a pH in the range from 6 to 8; and the highest output is achieved by culture with aeration and agitation for one to three days. It is needless to say that optimal culture conditions should be selected case by case according to the strain used and the composition of culture medium.

Restriction endonuclease Sse 8647I produced by the process of this invention is chiefly accumulated in the microbial cells. The grown cells can be isolated from the culture broth, for example, by centrifugation. The restriction endonuclease formed can be isolated and purified by using known techniques commonly employed for restriction endonuclease. For example, the collected microbial cells are dispersed in a buffer solution, and then broken down by ultrasonic treatment to allow extraction of the restriction endonuclease.

After removal of the cell debris by ultracentrifugation, for example, the supernatants thus obtained is dissolved in a buffer solution A (containing 20 mM Potassium phosphate, pH 7.5, 10 mM 2-mercaptoethanol and 5% glycerol) or solution B (containing 20 mM Tris-HCl, pH 7.5, 10 mM 2-mercaptoethanol), and the solution is dialyzed against the same buffer solution. The dialyzate is then purified by ion exchange chromatography, molecular sieve chromatography or affinity chromatography, thus giving the restriction endonuclease of this invention. For example, ammonium sulfate is added to the extract for salting out, the precipitate which is separated out is dissolved in a buffer solution A or solution B, and the solution is dialyzed against the same buffer solution. The dialyzate is then purified by ion exchange chromatography, molecular sieve chromatography or affinity chromatography, thus giving the restriction endonuclease of this invention.

The activity of this restriction endonuclease was determined according to the method described below.

A substrate solution of the composition shown in Table 2 below was prepared.

TABLE 2

| 10 mM | Tris-HCl, pH 9.1 |
|---|---|
| 10 mM | MgCl$_2$ |
| 7 mM | 2-Mercaptoethanol |
| 1.0 µg | Adenovirus-2 DNA |

This solution (48 µl) was preheated to 37° C., the sample of Sse 8647I (2 µl) to be tested was then added to allow the enzymatic reaction to proceed at that temperature, and the reaction was stopped ten minutes later by addition of 5 µl of a terminator solution (1% SDS, 50% glycerol, and 0.02% Bromophenol Blue).

The reaction mixture was applied to a 0.7% agarose slab gel, and electrophoresis was conducted at a constant voltage of 10 V/cm for about one to two hours. The buffer solution used for electrophoresis was 90 mM Tris-borate buffer containing 2.5 mM EDTA (pH 8.3). DNA bands can be detected by UV irradiation if 0.5 µg/ml ethidium bromide is previously added to the gel. Electrophoresis was regarded as complete when the number and intensity of the bands for DNA fragments no longer changed.

The restriction endonuclease activity which ensures complete digestion of 1 µg Adenovirus-2 DNA (produced by Bethesda Research Laboratories) after one hour's reaction at 37° C. was defined as one unit.

Restriction endonuclease Sse 8647I has the physicochemical properties as described below.

(1) Action and substrate specificity

This restriction endonuclease is capable of recognizing the nucleotide sequence of the following Chemical formula 1 in a double stranded DNA molecule and cleaving it at the sites marked by arrows.

Chemical formula 1

The nucleotide sequence recognized by restriction endonuclease Sse 8647I was determined as described below.

Restriction endonuclease Sse 8647I cleaved Adenovirus-2 DNA at eight sites, but failed to cleave λ-DNA, pUC18, M13mp18, SV40, Col E1, pBR322 and φX174 DNAs.

From the size of each digested DNA fragment, in addition to the cutting frequencies of the DNA molecules as described above, this restriction endonuclease was expected to recognize the nucleotide sequence of the following Chemical formula 2 in the DNA molecule.

Chemical formula 2

The nucleotide sequence of seven bases shown above includes five bases (Chemical formula 3) of Ava II restriction endonuclease recognition sequence.

Chemical formula 3

Therefore, one experiment was performed, in which Adenovirus-2 DNA were digested with Ava II before digestion with Sse 8647I. The resulting electrophoretic patterns of these DNA fragments were exactly same as those Sse 8647I single digestion. From these results, it was concluded that the restriction endonuclease Sse 8647I recognizes the nucleotide sequence shown in the Chemical formula 2.

To determine the cleavage position of Sse 8647I, M13 RF derivatives containing a Hpa I - Bgl II fragment of Adenovirus-2 DNA was constructed by inserting the fragment into the Sma I - Bam HI site of M13mp18 (produced by Takara Shuzo, Co., Ltd.). The nucleotide sequence of the Hpa I - Bgl II fragment described above including one recognition sequence of Sse 8647I was shown as SEQ ID NO:1. Single stranded DNA was prepared form the M13 RF derivative by the method generally used. The M13 primer M4 (produced by Takara Shuzo, Co., Ltd.) shown as SEQ ID NO:2 that binds to the site near the multicloning site of M13 RF was end-labeled with fluorescent compound at 5'-terminus. This primer was annealed with the single stranded DNAs prepared above, and extended by DNA polymerase from *Bacillus caldotenax* (BcaBEST DNA polymerase, produced by Takara Shuzo Co., Ltd.). The produced double stranded DNAs were digested with Sse 8647I, and the sizes of the digested DNA fragments were analyzed by denatured polyacrylamide gel electrophoresis. The products of the digestion reaction described above were detected as bands digested at the site indicated by an arrow in the following Chemical formula 4.

Chemical formula 4

5'-AGGACCT-3'

Moreover, the digestion product was converted to three base longer one by blunting the terminal with T4 DNA polymerase (produced by Takara Shuzo Co., Ltd.). From these experiments, it was concluded that Sse 8647I recognizes the nucleotide sequence shown in Chemical formula 1 and digests the DNA at the site indicated by an arrow in Chemical formula 4.

(2) Optimal conditions for enzymatic activity

I) Optimal temperature

The optimal temperature for Sse 8647I was approximately 30° C.

II) Optimal pH

The optimal pH for Sse 8647I was in the range from 7.5 to 9.5.

III) Salt concentration

The optimal salt concentration for Sse 8647I was in the range from 0 mM in the case of KCl or NaCl.

IV) $MgCl_2$ concentration

The enzymatic reaction of Sse 8647I was activated at a $MgCl_2$ concentration in the range from 5 mM to 20 mM.

(3) Determination of molecular weight

Molecular weight of Sse 8647I was determined for the native protein by equilibrium density gradient centrifugation. The density gradient was prepared by glycerol in the buffer solution as described in Table 3.

TABLE 3

| 10 mM | Tris-HCl, pH 7.5 |
|-------|------------------|
| 10 mM | 2-Mercaptoethanol |
| 100 mM | KCl |
| 10–25% | Glycerol |

In a 5 ml tube, 4.8 ml of continuous 10–25% (top to bottom) gradient was prepared, and the Sse 8647I protein in 200 µl of the same buffer was sedimented through the gradient. Marker proteins (SDS-PAGE molecular weight standard low range, produced by Bio-Rad Laboratories, Inc.) was sedimented through the same gradient, in parallel.

The gradient was centrifuged at 45,000 rpm at 4° C. for 21 hours in a swing rotor.

After centrifugation, fractions 250 µl were collected from the top of the gradient and fractions were numbered from 1 to 20.

These fractions were assayed for enzyme activity. The highest activity was detected in the fraction number 12. The sedimentation coefficient for the Sse 8647I protein was interpolated from the standard curve obtained from the analysis of marker proteins by SDS-PAGE after sedimentation.

An estimate of the approximate native molecular weight for Sse 8647I was calculated to be 60,000 to 75,000.

EXAMPLE

The following Example will further illustrate this invention but is not intended to limit its scope.

Example 1

(1) Preparation of Sse 8647I

The medium as shown in Table 4 was prepared. One flask of 100 ml volume containing 20 ml of the medium and four flasks of 2 l volume containing 500 ml of the medium were sterilized by the method generally used.

The strain Streptomyces sp. YH8647 (FERM BP-5022) was grown at 30° C. with shaking for 48 hours in the 100 ml flask described above. This culture was transferred to 2 l of flasks (5 ml each) and continued shaking at 30° C. for another 48 hours. These cultures were subjected to the refrigerating centrifugation and 43.3 g of cells were harvested.

TABLE 4

| Glycerol | 17.5 g |
|----------|--------|
| Polypeptone | 3.5 g |
| Meat extract | 3.5 g |
| Yeast extract | 3.5 g |
| NaCl | 2.0 g |
| $K_2HPO_4$ | 1.0 g |
| $MgSO_4$ | 0.5 g |
| Water | 1 l | pH 7.2–7.4

43.3 g of the microbial cells obtained above were suspended in 130 ml of buffer solution B (20 mM Tris-HCl, pH 7.5, 10 mM 2-mercaptoethanol), the suspension was treated in a ultrasonic crusher to break down the cell walls, and the resulting mixture was centrifuged (100,000×g, one hour) to remove the residue. To the supernatant (148 ml) thus obtained, was added KCl to 0.2M, the above solution was then adsorbed on 70 ml of phosphocellulose P11 (produced by Whatman Co.) packed in a column and previously equilibrated with buffer solution B containing 0.2M KCl. After washing with the same buffer as above, the adsorbed portion was eluted with buffer solutions B containing 0.2M to 0.8M KCl (linear concentration gradient technique).

The active fractions thus obtained were mixed together, the combined solution was dialyzed for four hours against buffer solution B, and the dialyzate was once more absorbed on 8.5 ml of DEAE-Cellose DE52 (produced by Whatman Co.) packed in a colum and previously equilibrated with buffer solution B. After thoroughly washing with the same buffer as above, the adsorbed portion was eluted with buffer solutions B containing 0M to 0.8M KCl (linear concentration gradient technique).

Further, the active fractions thus obtained were mixed together, the combined solution was dialyzed for four hours against buffer solution B, and the dialyzate was once more adsorbed on 2 ml of heparin Sepharose (produced by Pharmacia Biotech Inc.) packed in a column and previously equilibrated with buffer solution B. After thoroughly washing with the same buffer as above, the adsorbed portion was eluted with buffer solutions B containing 0M to 0.8M KCl (linear concentration gradient technique), affording the standard sample of restriction endonuclease Sse 8647I.

This standard sample was free from any non-specific deoxyribonuclease or phosphatase.

The purification method described above gave 600 unit activity from 43.3 g of wet microbial cells.

The present invention provides a novel restriction endonuclease capable of recognizing and cleaving a sequence of seven bases in double stranded DNA molecules. The endonuclease of this invention is of great use in the field of genetic engineering, for example, for analysis of long chain DNA molecules and for other purposes.

---

What is claimed is:

1. A purified restriction endonuclease, (a) which only recognizes a nucleotide sequence of the following Chemical formula 1 in double stranded deoxyribonucleic acid and only cleaves said nucleotide sequence at the sites marked by arrows,

Chemical formula 1 wherein A, G, T and C represent adenine, guanine, thymine and cytosine, respectively, and (b) which can be recovered from Streptomyces sp. YH8647 deposited under accession number FERM BP-5022.

2. The restriction endonuclease as defined in claim 1, which has the following physicochemical properties:

(a) Optimal temperature: approximately 30° C.;
(b) Optimal pH: 7.5 to 9.5; and
(c) Molecular weight: 60,000 to 75,000.

3. A process for producing a restriction endonuclease as claimed in claim 1, which comprises cultivating a strain belonging to the genus Streptomyces having all of the identifying characteristics of Streptomyces sp. YH8647 (FERM BP-5022) and which produces said restriction endonuclease, and recovering said restriction endonuclease from the culture broth.

4. A process for producing a restriction endonuclease as claimed in claim 2, which comprises cultivating a strain belonging to the genus Streptomyces having all of the identifying characteristics of Streptomyces sp. YH8647 (FERM BP-5022) and which produces said restriction endonuclease, and recovering said restriction endonuclease from the culture broth.

* * * * *